(12) United States Patent
Lipson

(10) Patent No.: US 7,266,401 B2
(45) Date of Patent: Sep. 4, 2007

(54) MEASURING ANALYTES FROM AN ELECTROMAGNETIC SPECTRUM USING A WAVELENGTH ROUTER

(75) Inventor: Jan Lipson, Cupertino, CA (US)

(73) Assignee: C8 Medisensors Inc., San Jose, CA (US)

( * ) Notice: Subject to any disclaimer, the term of this patent is extended or adjusted under 35 U.S.C. 154(b) by 337 days.

(21) Appl. No.: 10/923,264

(22) Filed: Aug. 20, 2004

(65) Prior Publication Data

US 2005/0124870 A1 Jun. 9, 2005

Related U.S. Application Data

(60) Provisional application No. 60/497,072, filed on Aug. 22, 2003.

(51) Int. Cl.
- *A61B 5/00* (2006.01)
- *G01J 3/44* (2006.01)
- *G01J 3/30* (2006.01)
- *G01J 3/42* (2006.01)

(52) U.S. Cl. ............ 600/316; 600/310; 356/317; 356/319

(58) Field of Classification Search ........... 600/316, 600/322, 310; 356/301, 326, 300, 302, 317, 356/319, 320, 328
See application file for complete search history.

(56) References Cited

U.S. PATENT DOCUMENTS

| | | | |
|---|---|---|---|
| 5,011,284 A | 4/1991 | Tedesco et al. | |
| 5,331,958 A | 7/1994 | Oppenheimer | |
| 5,370,114 A | 12/1994 | Wong et al. | |
| 6,122,052 A | 9/2000 | Barnes et al. | |
| 6,181,957 B1 * | 1/2001 | Lambert et al. | 600/319 |
| 6,868,285 B2 * | 3/2005 | Muller-Dethlefs | 600/317 |

FOREIGN PATENT DOCUMENTS

WO  WO 01/91632  *  6/2001

* cited by examiner

*Primary Examiner*—Eric F Winakur
(74) *Attorney, Agent, or Firm*—Fenwick & West LLP

(57) ABSTRACT

Weak signals scattered from analytes at multiple wavelengths can be summed to illuminate either a single detector or a multiplicity of detectors, offering the possibility of concentrating the spectral energy on a smaller total detector area. In addition, a method is disclosed whereby a calibration of the resulting signal for a given analyte can be obtained by means of measuring the quantity of water in the sample volume and by means of measuring the salinity of the fluid in the sample volume.

34 Claims, 8 Drawing Sheets

MEASURING ANALYTES FROM AN ELECTROMAGNETIC SPECTRUM USING A WAVELENGTH ROUTER

CROSS-REFERENCE TO RELATED APPLICATION

This application claims priority under 35 U.S.C. § 119(e) to U.S. Provisional Patent Application Ser. No. 60/497,072, filed Aug. 22, 2003.

BACKGROUND OF THE INVENTION

1. The Field of the Invention

This invention relates generally to measuring analytes in samples and, more specifically, to measuring analytes based on an electromagnetic spectrum that is characteristic of the analyte, for example as can be used to make non-invasive measurements of analytes in biological organisms.

2. Background and Relevant Art

Many attempts have been made to create appropriate apparatus for the non-invasive measurement of significant substances within biological organisms. The importance of such measurement capability arises not only from the need to observe biochemical reactions in such organisms without disturbance to the system but also in order to help control chronic diseases such as diabetes, where it is highly desirable to measure the patients blood glucose levels much more frequently than is practical, when puncturing the skin is required. Molecular spectroscopy has been proposed to make such measurements. However, the blood and interstitial fluids contain a very great number of compounds which must be distinguished. Absorption spectroscopy in the visible or near infrared suffers from the difficulty that the spectrum of many compounds that are present in the blood and other tissues substantially overlap in this region. Mid-IR spectroscopy produces spectra which are considerably more unique to individual molecules but suffers from two serious problems: (1) Detectors must be operated at cold temperatures if they are to be sufficiently sensitive, and (2) Water absorbs mid-IR radiation strongly and such radiation can only penetrate a few tens of microns into an organism.

Raman spectroscopy has been proposed to obviate some of these difficulties. In Raman spectroscopy, a scattering spectrum is produced at frequencies which are at the difference or sums of the frequencies of the illuminating radiation and the characteristic spectral frequencies of the molecule. Difference frequency generation is referred to as Stokes scattering, and sum frequency generation is referred to as Anti-Stokes scattering. The resulting spectral signatures are advantageously particular to the analytes of interest. However, the cross-sections for Raman scattering are small, and the resulting scattered signals are weak. Weak signals can also arise from spectroscopies that use other non-linear processes or where the available power from the light source is small. Other representative examples would include four wave mixing, frequency doubling, and multi-photon fluorescence.

U.S. Pat. No. 6,064,897, entitled "Sensor utilizing Raman spectroscopy for non-invasive monitoring of analytes in biological fluid and method of use," proposes the use of a multiplicity of bandpass filters and detectors to monitor a multiplicity of significant spectral lines emerging from the analyte of interest. The premise of the method is that a multiplicity of spectral lines is better correlated to any particular analyte than a single line, in the presence of other substances that may have confounding spectra. In addition, the patent presents a system using discrete transmission filters, which can have small attenuation. Such systems, however, may be limited in sensitivity by detector noise. The dark current of detectors scales adversely with increasing detector area. A multiplicity of detectors will therefore, in aggregate have approximately $N_d$ times the total dark current of an individual detector, where $N_d$ is the number of detectors. Because the dark current can be algebraically subtracted from the signal, the noise contribution arises from its variance, rather than from the mean value. The variance will be proportional to $(N_d)^{1/2}$. The approach, described in U.S. Pat. No. 6,064,897, therefore suffers from the difficulty that the aggregate noise scales with the number of detectors.

Raman scattering has also been proposed in the aqueous humor of the eye to measure glucose concentrations, as in U.S. Pat. No. 6,181,957. The aqueous humor has desirable optical properties such as high transparency. However, it is highly desirable to perform such monitoring through the skin so as to be able to continuously measure the relevant analytes. Also, serious issues of eye safety are entailed with the proposed method. Irrespective of the choice of measurement location, U.S. Pat. No. 6,181,957 also does not propose a method to resolve the problem of measuring weak scattered signals with practical detectors.

Raman scattering to measure multiple analytes in blood was reported in thesis work by T. W. Koo in a dissertation entitled, "Measurement of blood analytes in turbid biological tissue using near infrared Raman spectroscopy," published by MIT, in August 2001. Weak Raman signals are reported with as little as 6 counts per every 10 seconds for glucose. Long measurement times and high laser power is required (300 seconds, and 280 mW). These parameters are not practical for many applications.

In other work, glucose measurements were made, in vivo, using Raman scattering where light was introduced through the finger tip {"Noninvasive blood analysis by tissue modulated NIR Raman spectroscopy," J. Chaiken et al., in Proceedings of SPIE Vol. 4368, p. 134 (2001)}. The method improves the signal size but still uses cooled detectors, high laser power, and a low f number spectrometer that is expensive. The basic problem of weak signals remains unresolved.

Another difficulty, which has been of great importance in noninvasive measurements is the establishment of a reliable calibration for a wide variety of patients, that will remain valid over varying conditions and over time. Variations arise from many sources including the following: (1) Temperature, (2) Presence of varying concentrations of confounding substances with overlapping spectra, (3) Presence of other substances which affect the spectrum of the analyte either in regard to the amplitude, shape, or position of the spectral lines, (4) Variations in the location of the sampling, and in particular the fraction of blood, and interstitial fluid that may be therein, and (5) Drifts in the instrument including the wavelength of sources or of spectroscopic optical components.

Calibration has been sought through regression techniques, based on the spectra of multiple substances, obtained by measuring the individual amplitudes of many spectral lines. Such techniques remain sensitive to variations in the size and constituency of the sample volumes, and also result in much more complex spectrometers. The work of Chaiken et al. adds thereto a method based on subtracting signals using spectra obtained from a finger without pressure, with respect to a pressed finger. Referring to FIG. 11 of the aforementioned reference, there is still much scatter in the correlation between the Raman measurement and laboratory measurements of glucose, rendering the technique disadvantageously inaccurate.

BRIEF SUMMARY OF THE INVENTION

These and other limitations are addressed by an apparatus whereby weak signals at multiple wavelengths can be summed to illuminate either a single detector or a multiplicity of detectors, offering the possibility of concentrating the spectral energy on a smaller total detector area. In addition, a method is disclosed whereby a calibration of the resulting signal for a given analyte can be obtained by means of measuring the quantity of water in the sample volume and by means of measuring the salinity of the fluid in the sample volume.

In one aspect of the invention, a multiplicity of holograms is used to route the scattering wavelengths emerging from the sample to either a single detector or to more than one detector. In particular, the spectral energy emerging from the analyte to be measured generally appears in multiple spectral lines. Using the wavelength router, the energy in most or all of these spectral lines can be directed to a single detector, thus greatly increasing the signal to noise ratio for the measurement.

Further, the functionality of the router can be extended to combine the input energies of sources at multiple wavelengths, thus advantageously increasing the input optical power from a multiplicity of relatively inexpensive sources. Moreover, a portion of the power can be diverted to a reference cell, which is used to calibrate the measurement. The functionality of the router can be made general in that all or part of any input or output wavelength can be diverted to any of the appropriate locations or to multiple locations.

Another aspect of the invention concerns calibration techniques. As the analytes of interest are often dissolved in water, the quantity of a given analyte in the sample volume should scale as the quantity of water in the volume. The quantity of water is independently determined by measuring the amplitude of scattering signals at an appropriate Raman excited spectral line of water. By using a reference cell which contains water, the signal size can be calibrated absolutely to a specific quantity of water. In addition, it has been found that the absolute spectral location of a line of water will vary as a function of the quantity of free ions in the water. In particular, the line will shift in proportion to the concentration of sodium chloride, which is the dominant source of ions in most biological samples. The concentration of sodium chloride in human blood is held in a narrow range. Hence, the measurement can be assumed to be from a known fixed quantity, and an additional precise calibration is thereby obtained. The spectral shift, however, is quite small. Using the reference cell, which contains water without salt, and taking the difference signal at two advantageously chosen spectral positions, a precise determination is still possible. The reference cell can contain other materials, such as known concentration of analytes, to provide other types of calibration.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
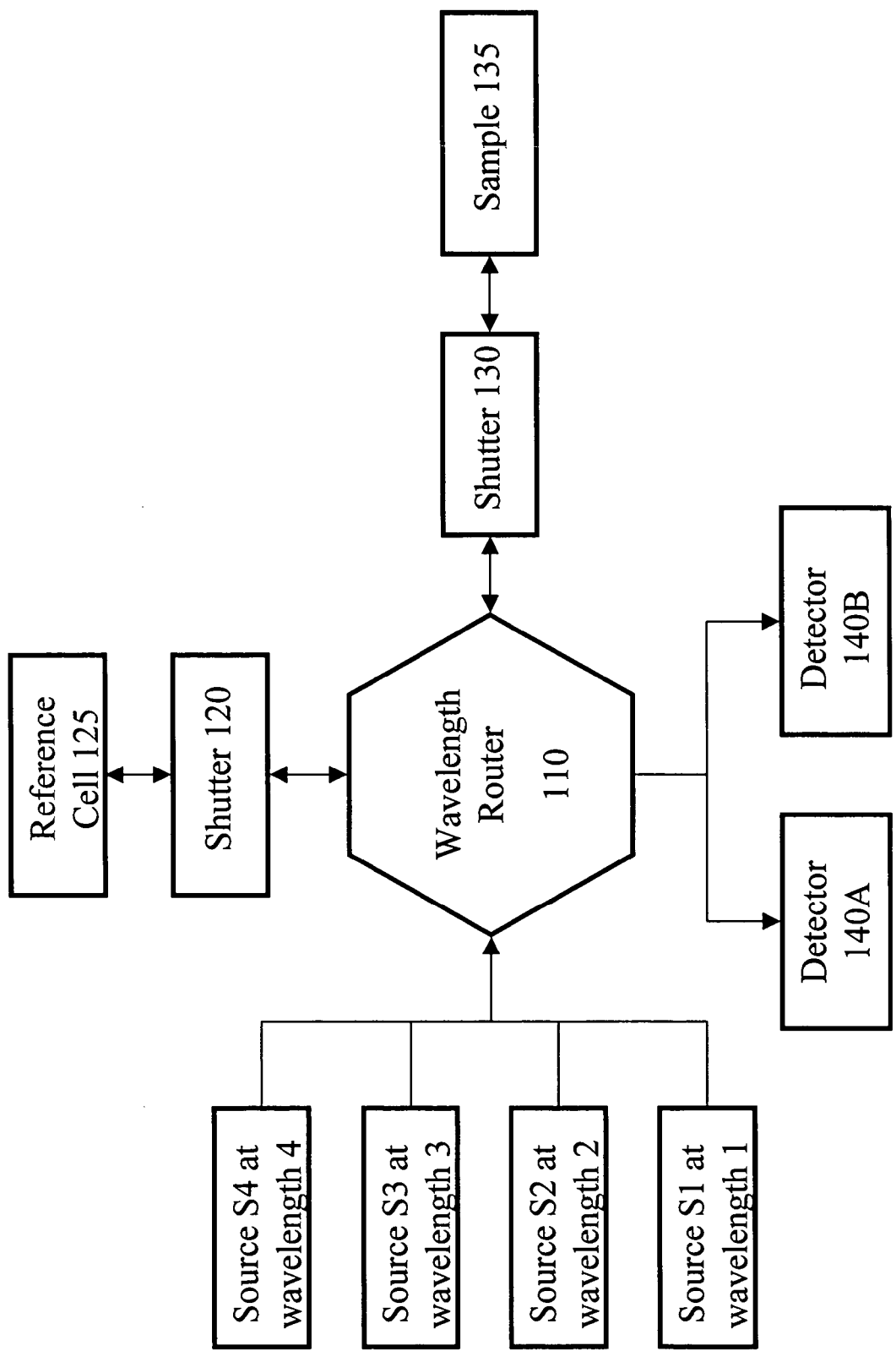
FIG. 1 is a block diagram of a device according to the invention.

FIG. 1 is a high-level block diagram of a device according to the invention, primarily showing the optical functionality of the major components within the device. In this particular example, the device includes four sources S1-S4, two detectors 140A-B, a reference cell 125 and shutter 120, a sample 135 and shutter 130, and a wavelength router 110.

Generally speaking, the device operates as follows. The sources S1-S4 produce light that is routed by the wavelength router 110 to the reference cell 125 and/or sample 135 via the respective shutter 120,130. The shutters 120,130 allow time gating of the illumination. Light scattered from the reference cell 125 and/or sample 135 is routed by the wavelength router 110 to the detectors 140.

The sources S1-S4 are shown as having a diversity of wavelengths (wavelengths 1-4 in FIG. 1). The wavelength router 110 directs a linear combination of the incident light from the sources S1-S4 via the shutters 120,130 to the sample 135 and/or to the reference cell 125. If $I_k$ is the intensity of the kth source, where each source is assumed to have a distinct wavelength, then the intensity $I_r$ that illuminates the reference cell 125 and the intensity $I_s$ that illuminates the sample 135 are given by:

$$I_r = \sum_{k=1}^{W} B_k I_k \qquad (1)$$

$$I_s = \sum_{k=1}^{W} A_k I_k \quad (2)$$

respectively, where $0 \leq A_k \leq 1$, $0 \leq B_k \leq 1$, and $A_k + B_k \leq 1$, and W is the total number of sources. The wavelength router 110 performs passive power splitting of the incoming light to the different outputs. The coefficients $A_k$ and $B_k$ describe the power splitting that occurs at wavelength k. In this example, there is a one to one correspondence between wavelengths and sources (i.e., source Sk produces light at wavelength k), but this is not required. The specific functionality can be chosen to route substantially all of a given wavelength to either the reference cell 125 or sample 135 by designing the wavelength router 110 so that the appropriate coefficient is nominally equal to 1 or 0.

Figure 2B:
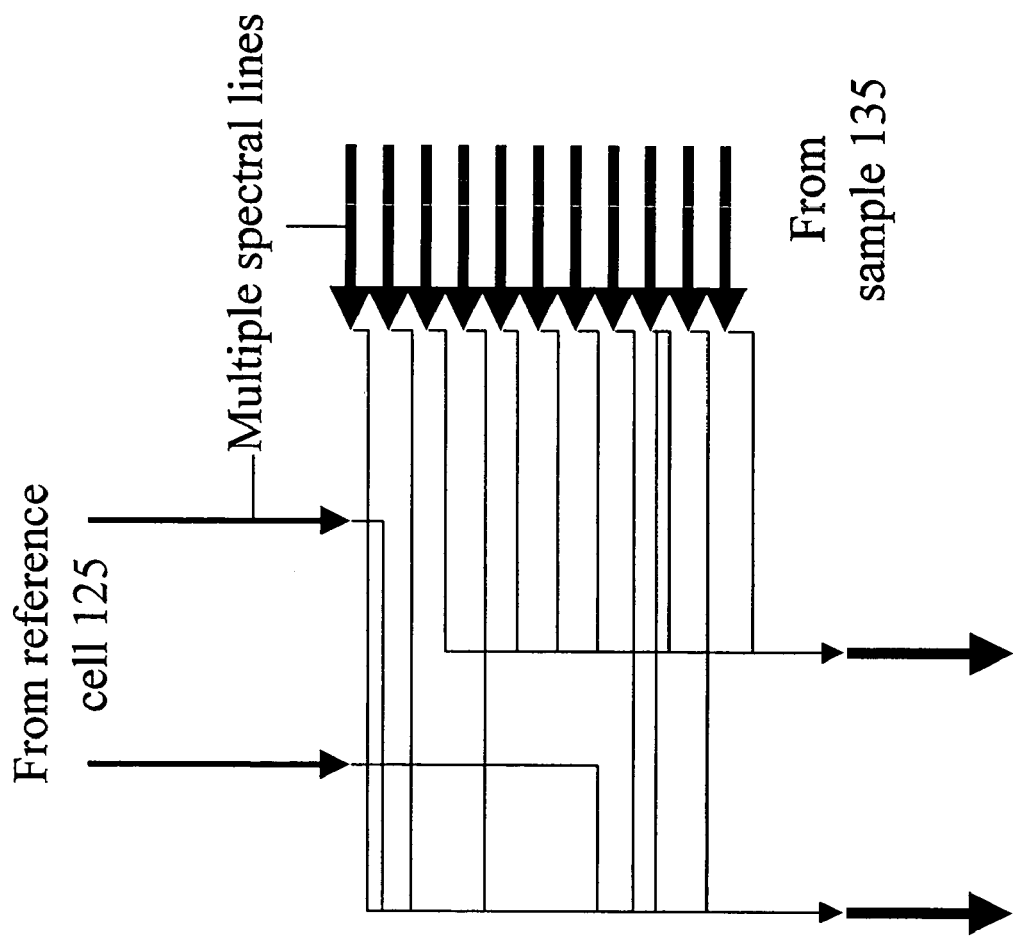
FIGS. 2a and 2b are diagrams illustrating wavelength routing by the wavelength router of FIG. 1.
Figure 2A:
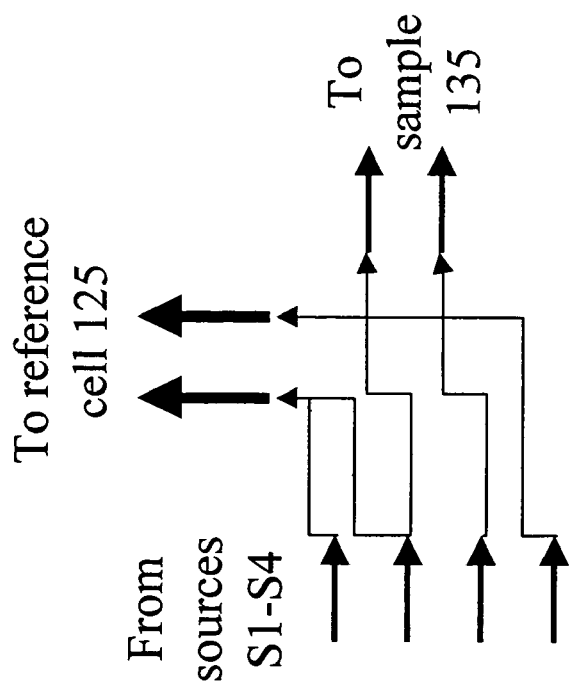

FIG. 2a is a diagram that shows the wavelength routing in a pictorial diagram. The four arrows on the lefthand side represent illuminating light produced by the four sources S1-S4. Each arrow represents a different wavelength. Each path from a source to a destination (either reference cell 125 or sample 135) represents a predetermined fraction of each input wavelength diverted to the appropriate destination. Light from sources S1, S2 and S4 is routed by the wavelength router 110 to the reference cell 125. Light from sources S2 and S3 is routed by the wavelength router 110 to the sample 135. In this diagram, each destination is also represented by arrows; the number of arrows is not meant to have a particular meaning for the destinations. The number of arrows also is not meant to imply characteristics about the physical location or direction of the optical beams. For example, a single arrow does not necessarily correspond to a single physical location or a single incident angle. The corresponding light could be contained in a single optical beam illuminating a single location, or a number of separate optical beams illuminating different locations and/or incident at different angles. In addition, light coming from a source may also be contained in multiple optical beams.

When light from the router 110 illuminates either the reference cell 125 or the sample 135, a scattering signal is generated. The signal typically consists of a multiplicity of spectral lines from the various substances within the reference cell 125 or the sample 135. Processes which generate these spectral lines include but are not limited to Raman scattering, second harmonic generation, third harmonic generation, four wave mixing and fluorescence. Any of these processes may produce a spectrum which is characteristic of the analyte to be measured. Each incident wavelength from a source can produce a multiplicity of scattered wavelengths by one or several of the above processes.

Taking Raman scattering as a particularly useful example, each incident wavelength will generate scattered wavelengths at frequencies which are given by the difference of the incident frequency and the characteristic Raman frequencies of the substance. This process is referred to as Stokes Raman scattering. Sum frequency generation also occurs and is referred to as Anti-Stokes Raman scattering.

In the following, the Stokes process is used to illustrate the function of this device but it is not limited to the Stokes process. If there are N incident wavelengths on the sample 135 and L characteristic Raman frequencies, then the scattered signal will contain N×L=P Raman scattered wavelengths. Each such wavelength may be routed to any of M detectors. As with the routing from source to reference cell/sample, the routing from reference cell/sample to detector is general and can be represented by the equation:

$$I_d = \sum_{k=1}^{P} C_{dk} P_k \quad (3)$$

where $I_d$ is the total power incident on the dth detector, $P_k$ is the scattered power at the kth scattered wavelength, and $C_{dk}$ is the fraction of the power at the kth wavelength diverted to the dth detector by the router 110. In the absence of optical amplification, conservation of energy requires that the coefficients $C_{dk}$ obey the following inequality for any of the individual scattered wavelengths $$\sum_{d=1}^{M} C_{dk} \leq 1 \quad (4)$$

and where $C_{dk} \geq 0$ for all values of d and k.

The function of the wavelength router 110 with respect to the scattered wavelengths from the sample 135 is shown in FIG. 2b, where each path represents the fraction of a given scattered wavelength diverted to a given detector. It is assumed in this example that there are five Raman lines of interest in the sample and the illuminating light is at two different wavelengths. Hence, there are a total of 2×5=10 scattered wavelengths from the sample. Each arrow on the righthand side represents one of the scattered wavelengths. It is assumed that there is one Raman line of interest in the reference cell. Hence, there are two scattered wavelengths from the reference cell.

In many applications, it is preferable that the routing scheme be a non-blocking architecture. The fraction of light that is diverted to a particular destination at a given wavelength is substantially independent of the fraction of light that is diverted at any other wavelength or to any other destination (subject to conservation of energy, of course). Mathematically, this means that the coefficients $C_{dk}$ need not be correlated for different values of k. Similarly, the coefficients $A_k$ need not be correlated and the coefficients $B_k$ need not be correlated. In many applications, it is also preferable that the architecture also permits broadcasting, which can be defined as the diversion of a fraction of a given wavelength to more than one destination. The resulting architecture therefore preferably can be a completely general linear non-blocking passive network with broadcast capability.

FIGS. 3-7 give further detail on preferred embodiments for the routing of source and signal wavelengths. Considerable progress has been made recently in the storage of data in holographic media. The purpose of such work was to maximize the number of independent holograms that could be stored in a given archival film. It is also possible to use such holograms as diffractive optical elements with narrow-band spectral properties. Because these media are stable and relatively thick (1 mm), it is possible to produce reflection holograms, which have substantial diffraction efficiency over <1 nm of wavelength in the near infrared. It is therefore possible to match the bandwidth of the hologram to that of the spectral line in question, thus efficiently diffracting only the desired signal. Narrow band holograms of this type are more readily obtained in reflection as opposed to transmission. Such holograms are not dichroic filters, which operate in transmission. In addition, these holograms operate independently. The aggregate filter function of two passband filters in series is the product of the individual filter functions. In contrast, the diffractive output of a multiplicity of holograms is essentially the sum of the diffraction from the individual holograms. This property makes it possible to construct complex, general routers, as the diffractive properties of each hologram may be considered to be substantially independent of the presence of other holograms.

Such holograms can be written by exposure to interfering writing beams of appropriate wavelength and angle of incidence. Upon exposure, the refractive index of the photosensitive material changes in proportion to the local intensity, maxima and minima corresponding to the constructive and destructive interference of the incident writing beams. Optimally engineered materials can respond with substantial index changes, and a large number of independent holograms can be written in the same volume. A multiplicity of such holograms can be used to construct a wavelength router, which deflects wavelengths according to the linear operations previously described.

Each hologram in general can be designed to divert a fixed fraction of the light within a predetermined bandwidth in the desired direction. Very high diffraction efficiency holograms can be written to divert >95% of the light, if substantially all of a particular wavelength is desired at a particular destination. Alternatively, it is possible to write several holograms of lower diffraction efficiency, each of which holograms is designed to divert substantially the same wavelength, but where each hologram is disposed at a different angle to divert some of the energy at any wavelength to several destinations.

While the routing scheme described is general, it is particularly advantageous when most of the spectral energy that is emitted from the analyte to be measured is focused onto a single detector. This is accomplished by diverting the preponderance of the P different scattered wavelengths onto a single detector. A large improvement in signal to noise ratio for the measurement of the desired analyte can thereby be obtained. Multiple analytes can be similarly treated, creating a spectrometer with very sensitive detection properties for several substances.

The number of high diffraction efficiency holograms that can be written in a given medium scales as follows:

$$N_H \propto n_1 T \qquad (4)$$

where $N_H$ is the number of holograms, $n_1$ is the maximum change in the index of refraction induced by photo-exposure, and T is the thickness of the medium.

For a reflection hologram to have >96% diffraction efficiency, the parameters must satisfy the following inequality:

$$v_r = \pi n_1 T/\lambda_a \cos \psi_o \geq 3\pi/4 \qquad (5)$$

where $\lambda_a$ is the wavelength of the incident radiation and $\Psi_o$ is the complement of the angle of incidence of the radiation with respect to holographic fringes ($\pi/2-\theta_0$), where $\theta_0$ is the angle of incidence. For small $\Psi_o$, $\lambda_a=0.9$ μm, and $n_1=0.02$, Eqn. 5 yields T>34 μm. In consequence, every high diffraction efficiency hologram that is written requires about 34 μm of photosensitive material, if the index difference is around 0.02.

In addition, it is necessary to also consider the spectral properties of the hologram. It is preferred that the hologram have appreciable diffraction efficiency over a range which is sufficient to diffract substantially all of the energy of the radiation that is desired to be deflected. In the case of routing the source wavelengths to their appropriate destinations, the hologram need only have high diffraction efficiency over a band larger than the spectral width of the source radiation. In the case of the scattered wavelengths, however, the hologram should diffract the minimum of radiation not associated with the line to be detected. In consequence, it is desirable to approximately match the band over which the hologram has high diffraction efficiency to the width of the spectral lines. Spectral lines have widths that can vary considerably and Raman lines can have spectral widths as small as 0.5 nm.

The following relationship governs the anticipated spectral width:

$$\xi_r = -\frac{\Delta\lambda}{\lambda_a}\left(\frac{2\pi n_o}{\lambda_a}\right)T\sin\theta_o = 3.9 \qquad (6)$$

where $n_o$ is the average refractive index of the medium and where the specified condition corresponds to the location in wavelength of the first null of reflectivity, and $\xi_r=3.9$ corresponds to a hologram which exactly meets the inequality (5). For reflection holograms of lower diffraction efficiency, the number on the right hand side of (6) is smaller but still >3 for a reflection hologram having diffraction efficiency of only 43%. Using Eqn. (6) shows that for a hologram to have a half width of 0.5 nm, for $n_o=1.55$, and angles of incidence near 90°, that T=650 μm.

The foregoing suggests that a preferred media for the holograms should be a photosensitive materials system of thickness not less than 100 μm and preferably approximately 1000 μm. It should be possible to create a change in the index of refraction of the medium by photo-exposure of not less than 0.005, and preferably 0.02. If the preferred parameters are obtained, then it is possible to achieve the objectives set forth in regard to diffraction efficiency and spectral width. It is further possible to write up to about 30 such holograms in a given volume.

It is sometimes desired to create holograms with broader bandwidth, while maintaining a thick medium that is capable of storing a multiplicity of high diffraction efficiency holograms. It is possible to cause either the period of the hologram or the background index of refraction to vary along a direction perpendicular to the fringes. By doing so, however, inequality (5) is no longer sufficient to guarantee high diffraction efficiency, and it is preferable to design with larger $n_1$ for each hologram. That reduces the total number of holograms that can be written before using up the total available index difference of the media. Nevertheless, it can be shown by simulation that in a 1000 μm thick medium, it is possible to write a hologram of >95% diffraction efficiency with a bandwidth of 2 nm and an index difference of 0.003. Hence, about six such holograms could be written in a medium that has a total index difference range of 0.02. In this example, the background index of refraction was varied linearly by a total of 0.003 from the front to the back of the hologram. The various types of holograms described in the foregoing examples are sufficient to create the essential functions of the wavelength router 110.

Figure 3B:
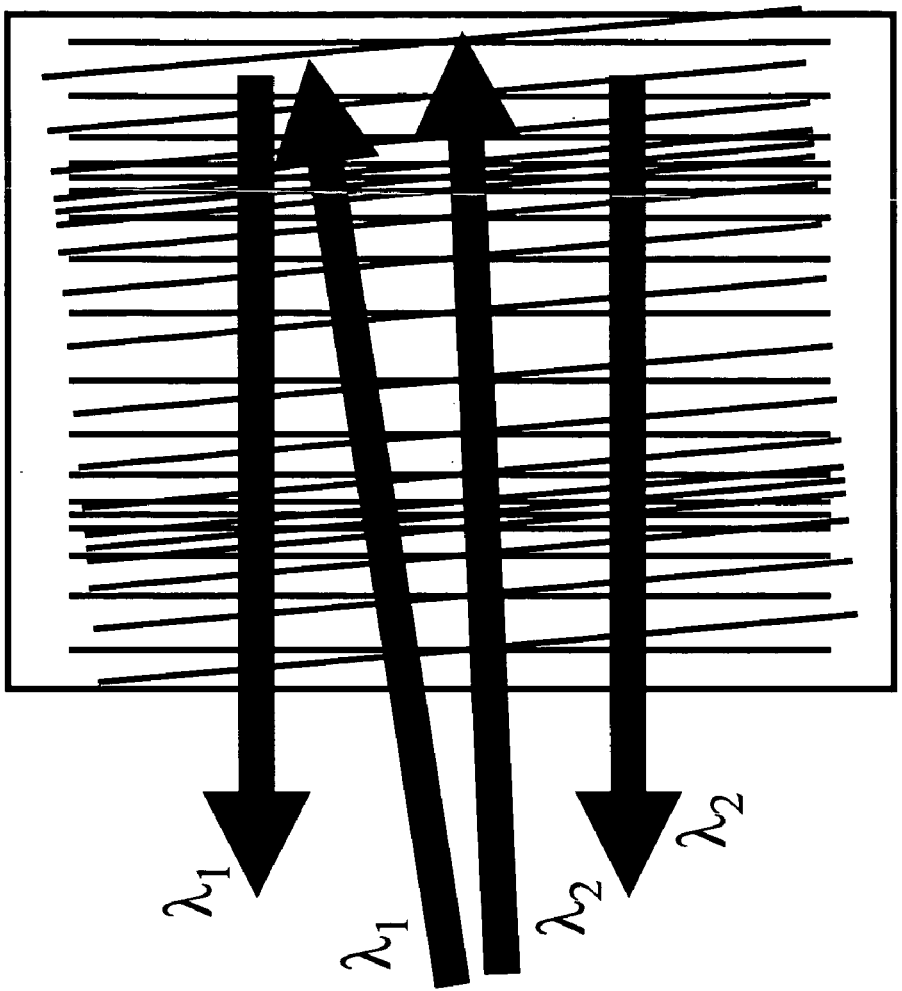
FIGS. 3a and 3b are diagrams showing the basic operation of reflection holographic optical elements (HOEs).
Figure 3A:
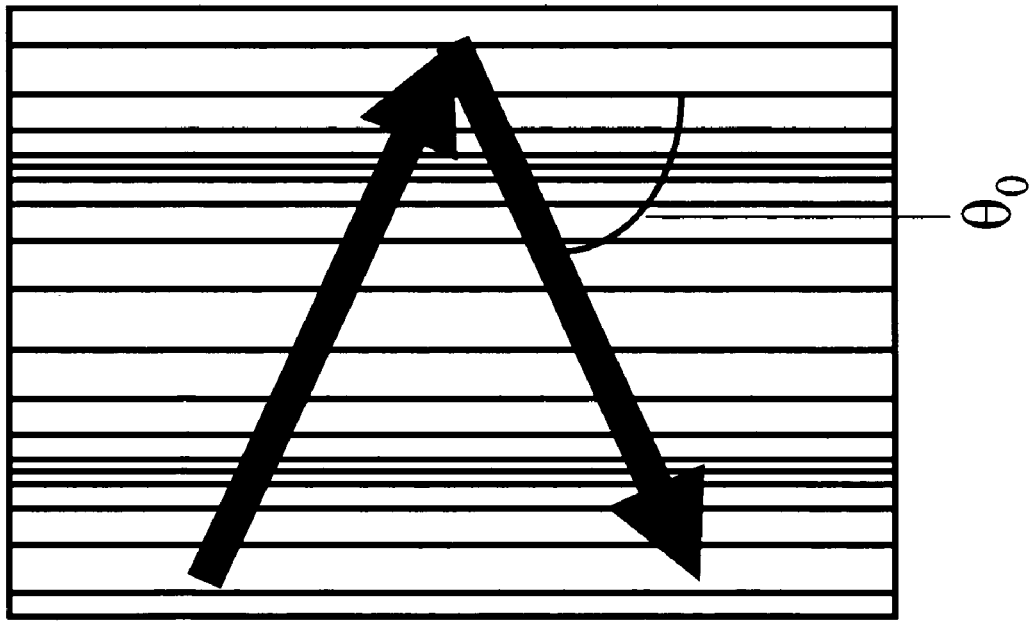

In this embodiment, the router is composed of holographic building blocks, which perform certain functions. One elementary function is to diffract light through an angle and the requisite hologram is shown in FIG. 3*a*. The index of refraction is represented by the frequency of the lines in FIG. 3*a*. The index of refraction change of the hologram is usually maximum where the beams used to perform writing have constructive interference (a medium in which the index changes negatively with exposure is also possible and works equivalently). FIG. 3b shows two holograms disposed at an angle in the same volume. If plane waves at two wavelengths are incident on this device at the appropriate angles, the plane waves will emerge at the same angle. This device is a wavelength muliplexer, and can be used to combine beams at a multiplicity of wavelengths. In the reverse direction it is a wavelength demultiplexer.

Figure 4:
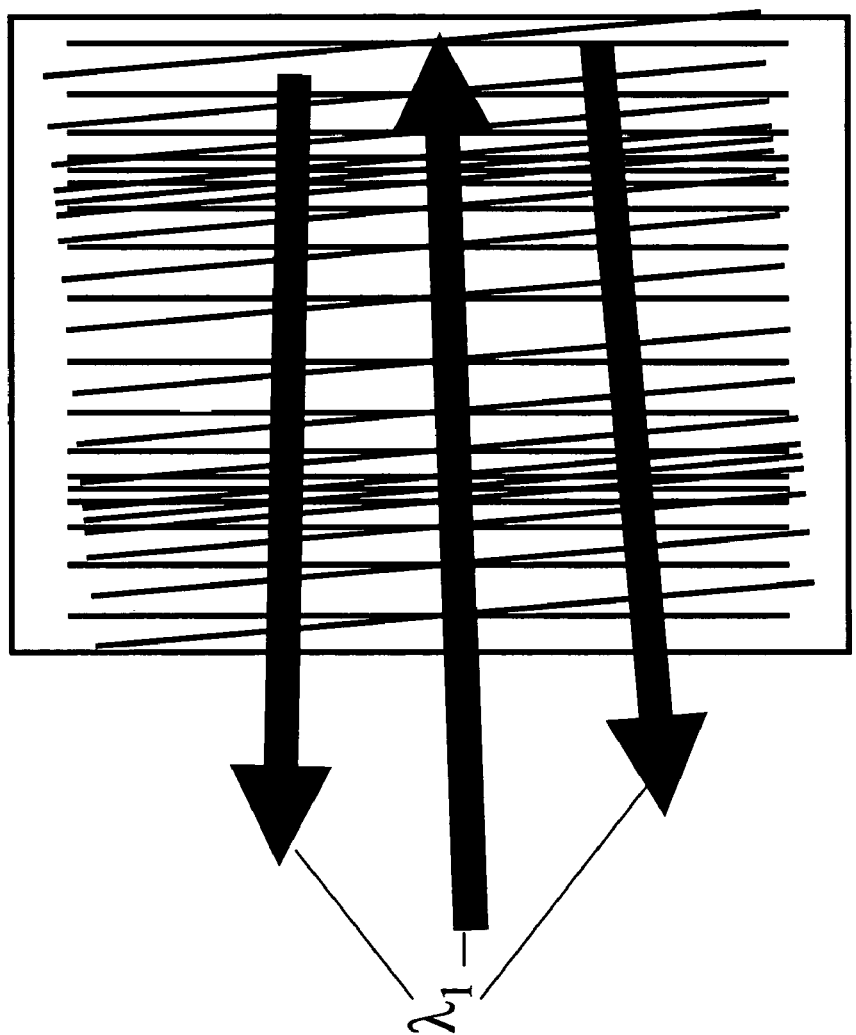
FIG. 4 is a diagram showing an HOE that splits incident light.

It is also possible to divert different fractions of a single wavelength into two different directions, the functionality being described as a splitter. The concept is illustrated in FIG. 4. Using a combination of the types of holograms described in the foregoing, it is possible to construct a wavelength router that can divert arbitrary fractional linear combinations of wavelengths to the desired destinations.

Figure 5:
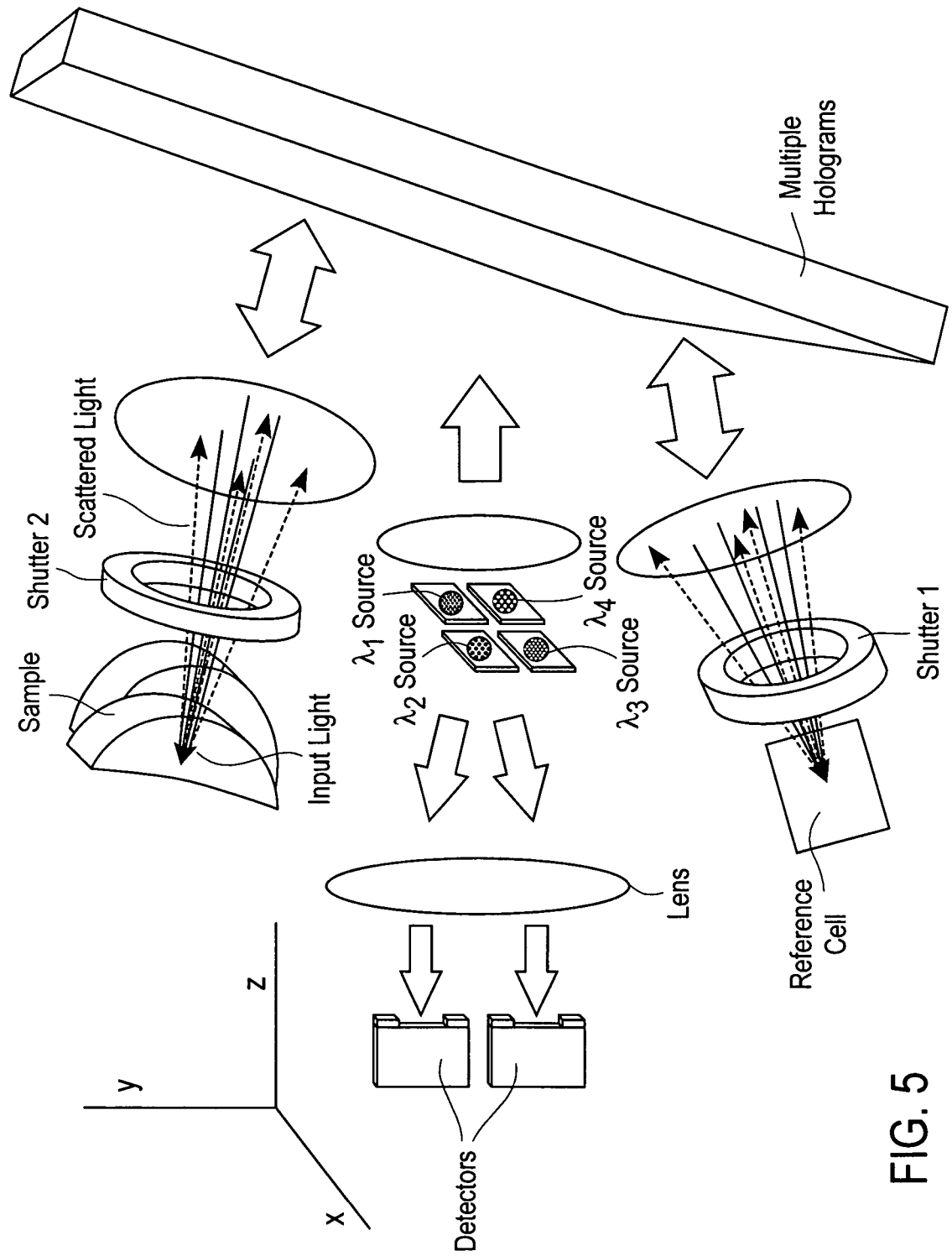
FIG. 5 is a drawing of one embodiment of a device according to the invention.

FIG. 5 is a drawing of a preferred embodiment, which can be considered to be composed of the following sub-assemblies:

1. Source assembly which consists in this example of sources of four different wavelengths and a collimating lens.
2. Holographic optical element (HOE) which consists of multiple reflection holograms, and performs the wavelength routing functions.
3. Sample and the associated beam delivery and collection optics.
4. Reference cell and associated beam delivery and collection optics.

The source assembly illuminates the HOE with nominally collimated light. Beams from each separate wavelength in the source emerge from the lens at a different angle. Appropriate holograms in the HOE reflect a portion of each of the separate beams in substantially the same direction. Hence, when they pass through a focusing lens, all beams will be focused at the same spot. The HOE also performs the function of splitting off a fixed fraction of each beam and diverting it either to the reference cell or the sample. All beams with a common destination emerge parallel from the HOE.

Upon being focused in the sample, the incident radiation will generate scattering at one or more wavelengths substantially different from that of the incident radiation, for each substance present in the sample volume. The scattered wavelengths are collected by the lens and directed back to the HOE. The HOE now routes an appropriate fraction of each scattered wavelength to a desired detector(s). A similar process transpires for the scattered wavelengths emerging from the reference cell.

Figure 6A:
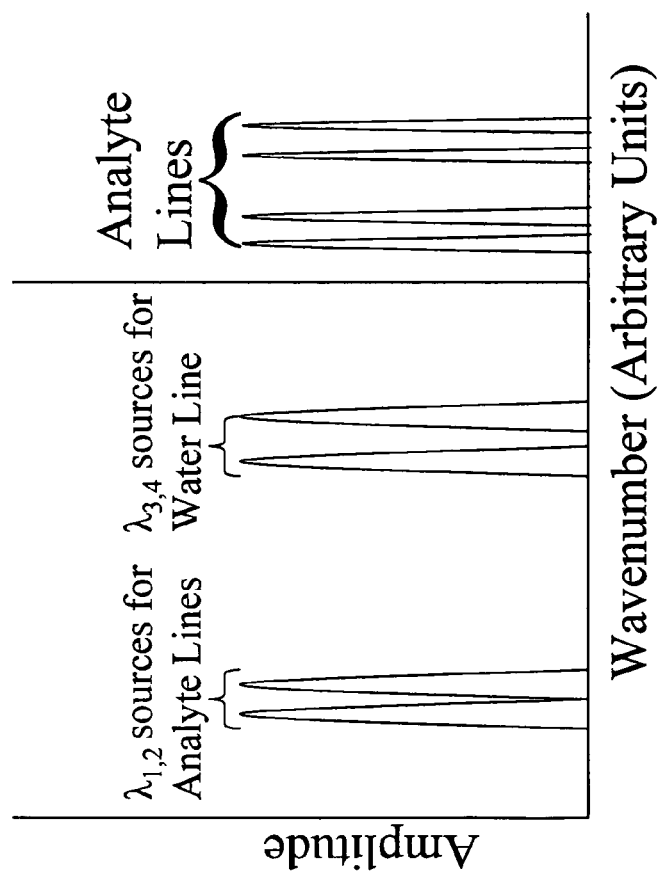
FIGS. 6a and 6b are spectral diagrams illustrating an example of the disposition of source wavelengths, spectral lines of an analyte, and wavelengths of holograms, for the device in FIG. 5.
Figure 6B:
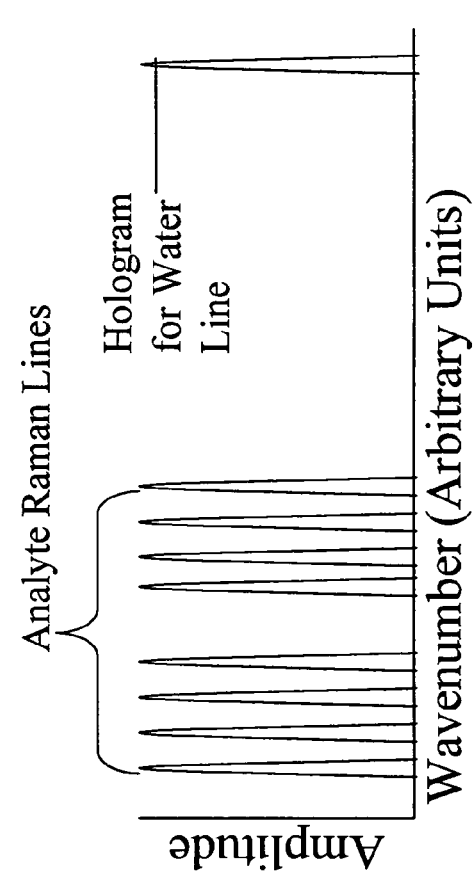

An example which illustrates the function of the HOE in FIG. 5 is presented in FIGS. 6a and 6b. In this example, four sources are used, labeled $\lambda_1$-$\lambda_4$ on the lefthand side of FIG. 6a. The two sources at $\lambda_1$ and $\lambda_2$ are used to generate Raman signals from four spectral lines of the analyte (the four spectral lines shown on the righthand side of FIG. 6a). There are therefore a total of eight difference frequency signals for the scattered light. FIG. 6b shows the spectral response of the HOE. Each of the eight spectral curves on the lefthand side of FIG. 6b represents a reflection hologram centered at one of the difference frequencies. Thus, the eight difference frequency signals are diverted by the HOE to the detector. The remaining two sources at $\lambda_3$ and $\lambda_4$ are used to measure the spectral line of water for calibration, as will be described in more detail below. After interaction with the sample/reference cell, both of these sources are shifted to the same wavenumber. A single hologram (the righthand spectral curve in FIG. 6b) diverts both signals to the detectors.

Calibration is an important feature of any device which is designed to make a quantitative measurement of the concentration of an analyte. In the example of FIG. 5, the analyte is assumed to be dissolved in a solvent. Many other substances may also be dissolved in the same volume of solvent. However, the quantity of the analyte is expected to be proportional to the volume of solvent from which light is collected. If all the water in the sample volume has the same concentration of the analyte, then the scattered signal from the analyte should be proportional to the scattered signal from the solvent. The ratio of the signal size from appropriate spectral lines of the solvent to the signal size from the appropriate lines of the analyte should be a measure of the concentration of the analyte. By measuring the solvent separately, and taking the aforementioned ratio, the measurement will become insensitive to changes in the sample volume which might arise from mechanical motion or physiological changes in an organism.

The reference cell preferentially contains, at minimum, a quantity of a solvent identical to the solvent in which the analyte is dissolved within the sample. As the geometry with respect to the reference cell can be regarded as strictly fixed and stable, the signal from the reference cell should be constant between repetitive measurements. Any changes will be due to drifts in optoelectronic components, and will thus be detected and extracted from the measurement.

The provision of a fixed standard internal to the apparatus allows a self-calibrating feature. In a preferred embodiment, the solvent contains one or more dissolved analytes, in precisely predefined concentrations. As with the solvent, the signals with respect to these analytes can only change due to component drifts. By making a measurement of the reference cell, the drifts may be mathematically extracted, thus the reference cell measurement permits an overall calibration of the apparatus.

In a preferred embodiment, which is applicable to noninvasive measurement of analytes in human tissue, an additional calibration is introduced which depends on the salinity of the bodily fluids. The concentration of sodium chloride in human blood is held in a very narrow range (approximately 6%) centered around 0.142 Moles/liter. The actual concentration can therefore be assumed to 0.142 Moles/liter. Salinity shifts the absolute wavelength of the O—H stretching spectral line of water by an amount proportional to the concentration of salt. The dependence is described in an article entitled, "Raman Spectroscopic Study of Sodium Chloride Water Solutions," by K. Furic et al., in the Journal of Molecular Structure, Volume 550-551, p. 225-234 (2000). The authors describe a procedure whereby the spectrum of water containing salt is mathematically subtracted from the spectrum of pure water in order to calculate the shift of the spectrum due to the presence of salt. The spectrum is measured at a minimum of two wavelengths.

Figure 6C:
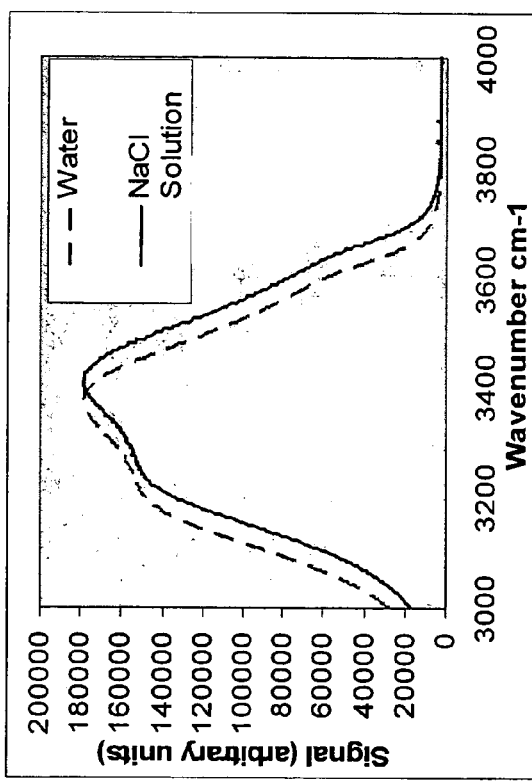
FIGS. 6c and 6d are spectral diagrams illustrating a calibration method for the device in FIG. 5 based on salinity measurements.
Figure 6D:
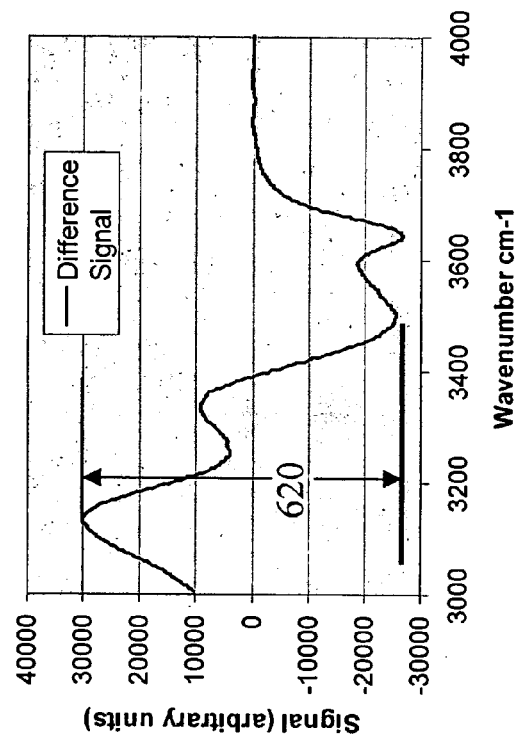

FIG. 6c shows the spectrum of water (the dashed line) and the spectrum of a solution containing sodium chloride (the solid line). FIG. 6d shows the difference signal between these two spectra. The difference signal reaches its largest positive amplitude at about 3140 cm$^{-1}$ and its largest negative amplitude at about 3506 cm$^{-1}$. The difference between the differential signal at these two wavelengths is marked by 620. It is a good measure of the wavelength shift due to the salinity and can be used to calcalculate the concentration of sodium ions in the blood.

In a preferred embodiment, the reference cell contains a quantity of salt free water and the spectrum is sampled at the two wavenumbers 3140 and 3506 cm$^{-1}$. These values have a nominal ratio and the actual readings are scaled mathematically to preserve this nominal value. The scaling factor is then applied to an identical measurement made using the sample rather than the reference cell. These measurements are used to estimate the salinity in the sample.

The mathematics is now described. Let $R_1$ be the signal measured at wavenumber 3140 cm$^{-1}$ in the reference cell and $R_2$ be the signal measured at wavenumber 3506 cm$^{-1}$ in the reference cell. The ratio $R_1/R_2$ is a fixed property of water once the wavelengths have been chosen. However, some variation may occur due to the differences in the optics or the two detectors used in the measurement. The value A is calculated such that $R_2'=A R_1$ and the ratio $A R_1/R_2'=1$.

The same measurement is applied to the sample, which has the shifted curve of FIG. 6c due to its salinity. If $S_1$ and $S_2$ are the signals obtained at the two wavenumbers 3140 and 3506 cm$^{-1}$ respectively from the sample, then the same factor, A, is applied to the signal $S_2$. Furthermore, the sums of the signals for the reference and sample preferably is scaled to be the same as follows:

$$R_1+AR_2=C(S_1+AS_2) \quad (7)$$

where C is a mathematical constant which is calculated to satisfy Eqn. 7. The mathematical function of Eqn. 7 is referred to as normalization.

The difference signals are $$D_1=R_1-CS_1 \quad (8a)$$

and $$D_2=AR_2-CAS_2 \quad (8b)$$

where now the quantity $(D_1-D_2)/R_1$ is proportional to the salinity of the sample. The constant of proportionality can be obtained by measuring a standard saline solution with the apparatus. The above algorithm can yield an additional calibration for all other analyte measurements as now signal amplitudes have been absolutely related to a known concentration.

It is desirable that light used for calibration traverse as much of the same optical path as the light from the sample as possible, and it is preferred that it be detected by the same detectors. In a preferred embodiment, the router diverts the water spectral lines to a single detector which is also the detector used to measure the sum of all powers in all the desired analyte lines. Referring to FIGS. 5, 6a, and 6b, the process for measurement of water is as follows:

1. Shutter 1 is opened and shutter 2 is closed so that only the reference cell is illuminated.
2. Source $\lambda_3$ is turned on to illuminate the reference cell. Scattered light is diverted by the corresponding hologram (i.e., the hologram designed for the particular wavelength(s)) and is measured in a single detector.
3. Source $\lambda_3$ is turned off and source $\lambda_4$ is then turned on. This source wavelength is chosen to satisfy the following relationship:

$$1/\lambda_3-1/\lambda_4=\Delta K_w \quad (9)$$

where $\Delta K_w$ the difference in wavenumbers between the two measurement wavelengths and is preferred to be approximately 366 cm$^{-1}$. As Stokes Raman scattering works on the basis of generating the difference frequency between the source and the characteristic vibrational frequency of the molecule, two sources obeying Eqn. 9 will generate a scattering signal which appears at the same wavelength, but which has sampled two distinct wavenumbers in the desired Raman line. In other words, the difference component between source $\lambda_3$ and wavenumber 3140 cm$^{-1}$ will be located at the same wavelength as the difference component between source $\lambda_4$ and wavenumber 3506 cm$^{-1}$. The same hologram as in step 2 will therefore divert the desired light to the same detector.

4. Shutter 1 is closed and shutter 2 is open such that the sample is measured.
5. Sources $\lambda_3$ and $\lambda_4$ are sequenced in the same manner as in the reference cell measurement, in order to make the sample measurement.
6. The results of the $\lambda_3$ and $\lambda_4$ measurements of the reference cell and sample are used to calibrate the salinity of the sample, as described above.

To measure the analyte, sources $\lambda_1$ and $\lambda_2$ are simultaneously actuated. In a preferred embodiment, the analyte is also present in the reference cell, and can be measured separately by opening shutter 1 and closing shutter 2. In this embodiment, the router deflects each scattered wavelength to the same detector. Hence, the power at each wavelength is summed. By opening shutter 2 and closing shutter 1, the same measurement can be performed for the sample. One advantage of using a multiplicity of sources is to obtain more source power from relatively inexpensive lasers. Note that this system permits a very large number of scattered wavelengths all to be deflected to a single detector. The signal increases proportionately. The variance of the dark current of the detector is independent of the signal. Hence, the S/N ratio with respect to dark current noise increases proportionately to the signal.

Because the concentration of the analyte in the reference cell is known, the signal from the reference cell is a good calibration for the signal from the sample. In the case when more than one analyte is to be measured, a preferred embodiment consists of adding additional detectors for each analyte and of adding each analyte to the solution in the reference cell.

The presence of the sources, sample, reference cell and detectors on the same side of the optical system with respect to the HOE can produce crowding. This can be somewhat ameliorated by moving one or more assemblies out of the plane of the drawing (along the x direction referring to FIG. 5). Nevertheless when compactness is critical, a problem of crowding can still arise.

The issue arises from the dependence of the acceptance angle of the holograms as a function of the incident angle. For reflection holograms, the angular deviation $\delta$ from nominal for which the diffraction efficiency will go to zero is given by:

$$\delta = \frac{\Delta\lambda}{\lambda_a}\tan\theta \quad (10)$$

where $\Delta\lambda$ is the wavelength deviation from nominal which causes the diffraction efficiency to go to zero. Note that this calculation emerges from a first order expansion of the Bragg condition, and as $\theta$ approaches 90°, it is preferable to carry out the expansion to second order as the first term vanishes. If the hologram is to have a narrow wavelength band, which is optimal for narrow spectral lines from the analytes, it will also have a narrow field of view unless the incident angle is relatively close to $\pi/2$ radians. The angular diversion between the incident and diffracted light is just 2 $(\pi/2-\theta)$, which becomes small as $\theta$ becomes large.

For collimated light incident on a lens of focal length f, the translation deviation between the spot emitting the light and the spot in which scattered light is focused is $2f(\pi/2-\theta)$ which also becomes small. Hence, sources and detectors would be crowded together unless the focal lengths are large. The optical system, however, preferably collects as large a fraction of the light emanating from the sample as possible. In addition, it is undesirable to magnify the size of the spot in the sample because then larger detectors would be required, which would have higher dark current. As a result, the size of the optics scale with the focal length. Hence, in the design of FIG. 5, the relief of crowding typically results in larger optics.

Figure 7:
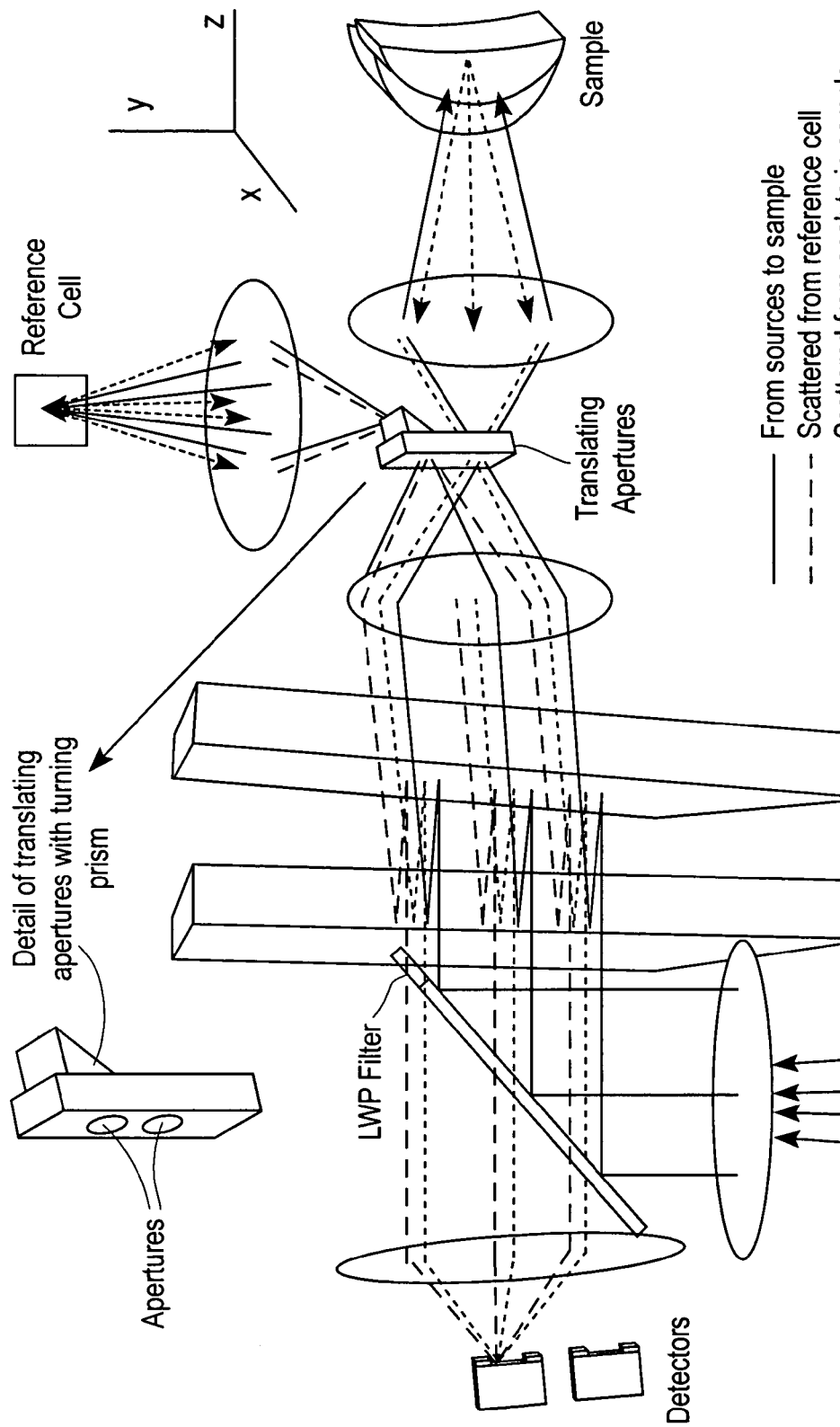
FIG. 7 is a drawing of a compact embodiment of a device according to the invention.

A solution to the problem of crowding for compact devices is presented in FIG. 7. Here a second HOE is introduced. The second HOE performs the function of reflecting substantially all of the radiation incident upon it from the reflections arising from HOE1. HOE2 is disposed at an angle with respect to HOE1. In consequence, light propagating back from HOE2 towards HOE1 is outside the field of view of the holograms in HOE1 and is not diffracted a second time by HOE1. Such an arrangement is possible because the field of view of the hologram, $\delta$ can be much smaller than the angle through which the light is diverted and hence the light will not be diffracted a second time.

As a result, the source can be on the opposite side of the system from both the sample and reference cell. A long wave pass filter (LWP) is used to reflect source light while passing the scattered light to the detectors. This arrangement is appropriate for Stokes Raman Scattering. For Anti-Stokes Raman scattering, a short wave pass filter should be chosen. Aside from further relieving the crowding, the filter also helps deflect source light that might be scattered off of the optics, or other index discontinuities in the optical path, from reaching the detectors.

To preferentially illuminate either the sample or reference cell, a moveable dual aperture with reflecting prism is employed. When it is desired to illuminate the sample, the device is positioned in the Y direction (see FIG. 7 for axis definitions) such that focused light from the sources and focused light from the scattering passes through the lower of the two apertures. To illuminate the reference cell, the dual aperture with turning prism is translated in Y such that the light passes through the upper aperture. FIG. 7 shows the apertures in this position. Rays which are shown that traverse the apertures in the direction of the sample are presented to show the path of the source and scattered light when the light passes through the lower aperture. The prism deflects both source and scattered light through approximately 90°, allowing the reference cell to be disposed away from the sample.

In FIG. 7, marginal and central rays are presented for the illumination and scattering signals. Angles have been exaggerated for clarity. Rays which are at slightly different Y positions have been positioned so as to be visible in the drawing and can in practice overlap. Some rays that would exist between the two HOE's have been suppressed so as not to produce an excessively tangled view of the rays between the HOE's.

FIG. 7 shows a case where the scattered light from both the reference cell and sample would be brought back to a single detector but that is not a requirement of the design. It is possible to combine the functions of HOE1 and HOE2 in a single medium. The two functions have been separated here for clarity of presentation.

What is claimed is:

1. An apparatus for the measurement of the optical spectra of analytes within a sample, and comprising all of the following:
   one or more sources of optical radiation;
   a first passive wavelength router which can divert a fractional linear combination of powers at different wavelengths of the optical radiation from the one or more sources to a sample containing an analyte, the analyte scattering the optical radiation in multiple spectral lines;
   a second passive wavelength router that directs a fractional linear combination of the power in each of the scattered spectral lines from the analyte to a detector, wherein the second passive wavelength router comprises a holographic optical element storing at least two holograms, each hologram directing a least a portion of a different scattered spectral line to the detector.

2. The apparatus of claim 1 wherein each source has a wavelength distinct from all other sources.

3. The apparatus of claim 1 where the holograms are reflection holograms.

4. The apparatus of claim 1 wherein the first passive wavelength router comprises a holographic optical element storing at least two holograms.

5. The apparatus of claim 4 where the holograms are reflection holograms.

6. The apparatus of claim 1 in which at least two of the scattered spectral lines emanating from the analyte are routed to one detector.

7. The apparatus of claim 1 in which at least two of the scattered spectral lines from a multiplicity of analytes are routed to a multiplicity of detectors, each detector receiving only the scattered spectral lines from a single analyte at any instant in time.

8. The apparatus of claim 1 where one of the analytes is glucose.

9. The apparatus of claim 1 where the sample is comprised of human tissue.

10. The apparatus of claim 1 where the sample is comprised of human blood.

11. The apparatus of claim 1 wherein at least one of the wavelength routers comprises at least two reflection holograms, both of which diffract a fraction of the light within a wavelength band such that the some or all of the light within the band emerges from the pair of holograms in a direction that differs from the direction of the incident light by more than ninety degrees.

12. An apparatus for making a calibrated measurement of a concentration of an analyte dissolved in water within a sample comprising the following:
   one or more sources of optical radiation;
   a passive optical system which provides a means of transmitting the radiation from at least one of the sources to the sample, and of collecting at least one spectral line from the scattered signal of an analyte within the sample;
   at least one detector which detects the scattered signal from the analyte;
   at least one detector which need not be different from the detector or detectors used to detect scattered light from the analyte, to collect scattered light from at least one spectral line of the water in the sample, the amplitude of said spectral line being used as a calibration factor in calculating the concentration of the analyte in the sample; and a processing device, wherein the processing device determines the salinity of the water by the shift of at least one of the spectral lines of the water, and where the sample is composed of biological material where the normal range of the salinity is not larger than 25%, such that the nominal value may be assumed to be present, and where then said salinity measurement constitutes an additional calibration parameter for the concentration of one or more analytes.

13. The apparatus of claim 12 in which the biological material is human tissue.

14. The apparatus of claim 13 in which the human tissue is blood.

15. The apparatus of claim 13 in which the human tissue is interstitial fluid.

16. The apparatus of claim 12 in which at least one of the analytes is glucose.

17. The apparatus of claim 12 where one of the sources operates at a wavelength such that a spectral line of the water in which the analyte is dissolved within the sample will be directed at the same detector that is used for the measurement of at least one line of the analyte, using one or more holograms in the passive optical system that is used to divert that specific line of the analyte to said detector.

18. An apparatus for making a calibrated measurement of the concentration of an analyte dissolved in a solvent within a sample comprising the following:
  one or more sources of optical radiation;
  a reference cell containing a quantity of solvent, said solvent being identical to the solvent in which the analyte is dissolved within the sample;
  one or more detectors; and
  a passive optical system that directs the optical radiation from the one or more sources to the sample and also to the reference cell containing the solvent, and that further directs a linear combination of spectral lines scattered from the solvent in the sample to the one or more detectors, wherein the detectors produce a second signal corresponding to the solvent spectral lines from the sample and a third signal corresponding to the solvent spectral lines from the reference cell.

19. The apparatus of claim 18, in which the analyte to be measured is additionally present in the solvent of the reference cell, and the passive optical system further directs a linear combination of spectral lines scattered from the analyte in the sample to the one or more detectors and directs a linear combination of spectral lines scattered from the analyte in the reference cell to the one or more detectors, wherein the detectors further produce a first signal corresponding to the analyte scattered spectral lines from the sample and a fourth signal corresponding to the analyte scattered spectral lines from the reference cell.

20. The apparatus of claim 19 in which at least one of the analytes is glucose.

21. The apparatus of claim 18 in which the solvent is water.

22. The apparatus of claim 21 in which at least one of the analytes is glucose.

23. The apparatus of claim 18 in which the sample comprises biological material.

24. The apparatus of claim 18 in which the sample comprises human tissue.

25. The apparatus of claim 24 in which the sample comprises human blood.

26. The apparatus of claim 25 in which at least one of the analytes is glucose.

27. The apparatus of claim 24 in which at least one of the analytes is glucose.

28. The apparatus of claim 18 in which the sample comprises human interstitial fluid.

29. The apparatus of claim 28 in which at least one of the analytes is glucose.

30. The apparatus of claim 18 in which at least one of the analytes is glucose.

31. The apparatus of claim 18, further comprising a processing device, wherein the processing device determines the salinity of the water in the sample from the shift of a Raman spectral line of the water from the nominal value without the presence of salt
  by a comparison between the location of a Raman spectral line of water in the reference cell and in the sample.

32. The apparatus of claim 31 wherein the processing device produces a calibration factor based on signals generated by the detectors, the calibration factor used to calculate a concentration of the analyte in the sample.

33. The apparatus of claim 18 in which the passive optical system further comprises a moveable opaque or high reflecting material with at least a first and second aperture, and the passive optical system produces the following foci:
  a) focus for optical radiation being directed from the one or more sources toward the sample;
  b) focus for scattered spectral lines from the sample being directed toward the one or more detectors;
  c) focus for optical radiation being directed from a source toward the reference cell;
  d) focus for scattered spectral lines from the reference cell being directed toward the one or more detectors;
  wherein
  the foci in a) and b) are in a first substantially same location, and the foci in c) and d) are in a second substantially same location,
  and the first and second apertures can be translated in such a way that the foci of a) and b) are transmitted through the first aperture and can be translated in such a way that the foci of c) and d) are transmitted through the second aperture.

34. The apparatus of claim 33 further comprising a prism to deflect radiation passing through at least one of the first and second apertures through an angle of at least ten degrees.

* * * * *